United States Patent
Glazier et al.

(10) Patent No.: US 8,137,399 B2
(45) Date of Patent: Mar. 20, 2012

(54) IMPLANTABLE PRISMATIC DEVICE, AND RELATED METHODS AND SYSTEMS

(75) Inventors: Alan N. Glazier, Rockville, MD (US); Robert S. Winsor, Round Hill, VA (US)

(73) Assignee: Vision Solutions Technologies, Inc., Rockville, MD (US)

( * ) Notice: Subject to any disclaimer, the term of this patent is extended or adjusted under 35 U.S.C. 154(b) by 1628 days.

(21) Appl. No.: 11/102,807

(22) Filed: Apr. 11, 2005

(65) Prior Publication Data

US 2006/0229720 A1   Oct. 12, 2006

(51) Int. Cl.
A61F 2/16 (2006.01)

(52) U.S. Cl. .............. 623/6.26; 623/6.13; 623/6.34

(58) Field of Classification Search ........... 623/6.26, 623/6.13, 6.32–6.35, 6.27, 6.28
See application file for complete search history.

(56) References Cited

U.S. PATENT DOCUMENTS

| | | | | |
|---|---|---|---|---|
| 4,074,368 A * | 2/1978 | Levy, Jr. et al. | 623/6.13 |
| 4,581,031 A | 4/1986 | Koziol et al. | |
| 4,731,078 A * | 3/1988 | Stoy et al. | 623/6.13 |
| 4,828,558 A * | 5/1989 | Kelman | 623/6.13 |
| 5,201,762 A * | 4/1993 | Hauber | 623/6.34 |
| 5,222,981 A * | 6/1993 | Werblin | 623/6.34 |
| 5,443,506 A * | 8/1995 | Garabet | 623/6.13 |
| 5,683,457 A | 11/1997 | Gupta et al. | |
| 5,728,156 A | 3/1998 | Gupta et al. | |
| 5,782,911 A * | 7/1998 | Herrick | 623/6.26 |
| 5,800,532 A * | 9/1998 | Lieberman | 623/6.26 |
| 5,928,283 A * | 7/1999 | Gross et al. | 623/6.34 |
| 6,204,975 B1 * | 3/2001 | Watters et al. | 359/633 |
| 6,559,317 B2 * | 5/2003 | Hupperts et al. | 548/263.2 |
| 6,855,164 B2 | 2/2005 | Glazier | |
| 7,144,423 B2 * | 12/2006 | McDonald | 623/6.27 |
| 7,229,476 B2 * | 6/2007 | Azar | 623/6.26 |
| 7,842,086 B2 * | 11/2010 | Dotan et al. | 623/6.17 |
| 2004/0117013 A1 * | 6/2004 | Schachar | 623/6.36 |
| 2004/0138746 A1 * | 7/2004 | Aharoni et al. | 623/6.35 |
| 2005/0071002 A1 * | 3/2005 | Glazier | 623/6.13 |

* cited by examiner

*Primary Examiner* — Paul Prebilic
(74) *Attorney, Agent, or Firm* — Berenato & White, LLC

(57) ABSTRACT

An intraocular device including a prism and shift amplifier is provided. Also provided is a system containing the intraocular device, and a method for improving vision of a person with central vision loss. The method involves implanting the intraocular device in the person so that the prism and shift amplifier cumulatively shift a retinal image away from the fovea of an eye to a functional retinal portion of the eye. Also provided is a method for correcting a binocular misalignment of a person using the intraocular device.

17 Claims, 4 Drawing Sheets

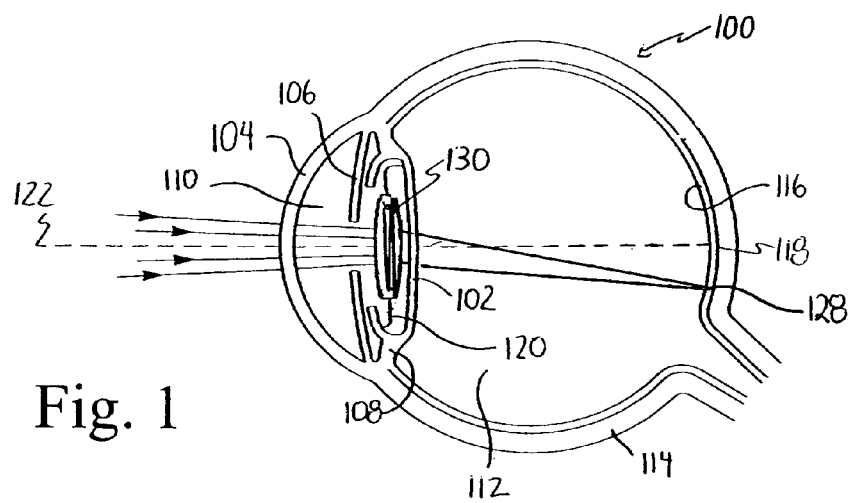
Fig. 1
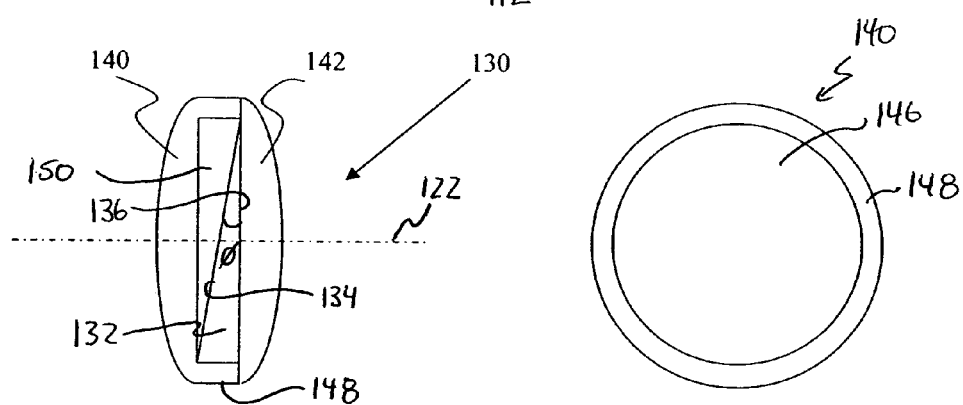 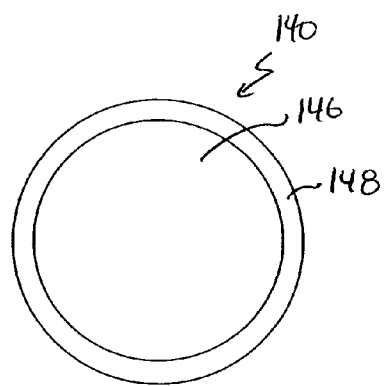
Fig. 2    Fig. 3
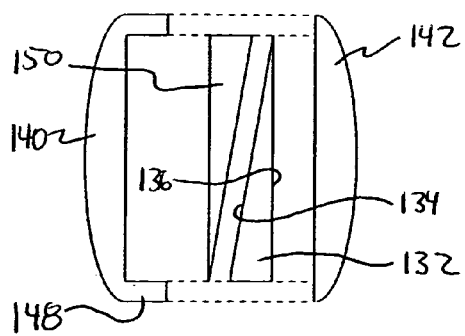 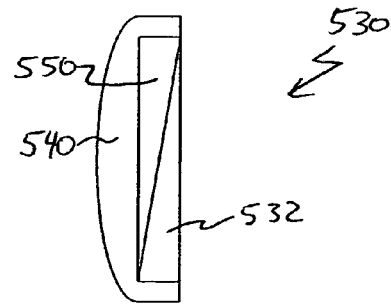
Fig. 4    Fig. 5

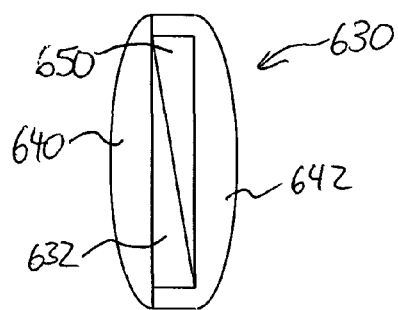
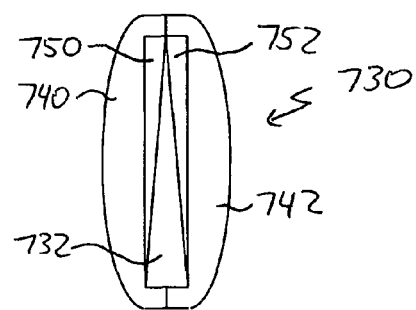
Fig. 6   Fig. 7
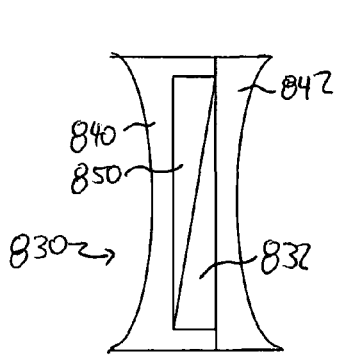
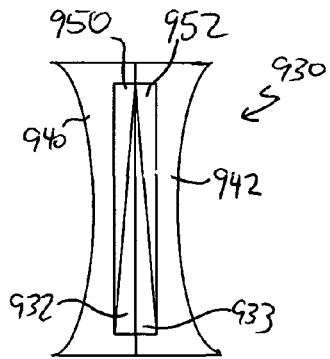
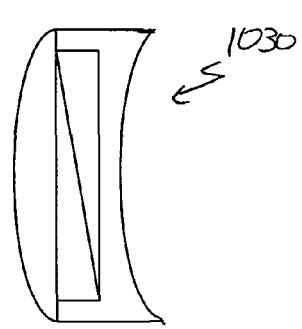
Fig. 8   Fig. 9   Fig. 10
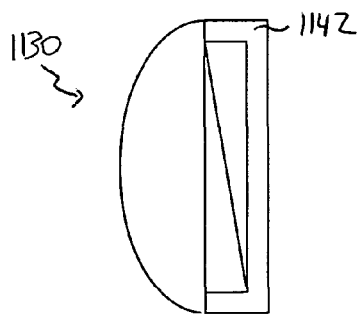
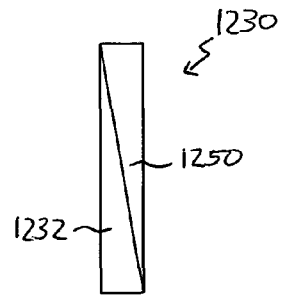
Fig. 11   Fig. 12

IMPLANTABLE PRISMATIC DEVICE, AND RELATED METHODS AND SYSTEMS

BACKGROUND OF THE INVENTION

1. Field of the Invention

The present invention relates to prismatic intraocular devices and related methods and systems for using such devices to improve, and more desirably restore vision. In a particularly preferred embodiment, the devices and related methods and systems are useful for patients having central field vision loss, such as encountered with degenerative retinal conditions, including but not limited to age-related macular degeneration, diabetic macular edema, lebers optic neuropathy, myopic macular degeneration, retinitis pigmentosa, and the like. In another preferred embodiment, the devices and related methods and systems are useful for patients having binocular misalignment, such as esotropia, exotropia, and vertical imbalances.

2. Description of the Related Art

Retinal degenerative conditions (RDCs) adversely affect eyesight and often lead to partial or complete blindness. An RDC such as macular degeneration leaves the afflicted individual with "blind spot" or scotoma usually at or near the center of a person's visual field. The blind spot or scotoma may appear as a black, gray, or distorted image. Objects in the central field of vision falling within the scotoma are not visible, thus permitting the afflicted individual to view only peripheral images around the blind spot. The visual field provided by such peripheral images is often insufficient to allow the individual to perform routine activities such as reading, driving a vehicle, or even daily chores and errands. For example, when an individual having a RDC attempts to recognize another person at a distance, the individual may be able to discern the eccentric body portions of the viewed person peripherally, but the scotoma may "wipe out" the facial details of the viewed person, rendering the person unrecognizable.

To understand RDCs, it is necessary to have a basic understanding of the human eye and the afflictions that lead to RDCs. Generally, the most outwardly visible structures of the human eye include an optically clear anterior cornea, the iris sphincter sitting behind the cornea, and the pupil, which is an aperture defined by the inner rim of the iris. The pupil appears as a circular opening concentrically inward of the iris. A physiological crystalline lens in a capsular bag is positioned posterior to the iris. Ciliary muscle concentrically surrounds the capsular bag, and is coupled to the physiological crystalline lens by suspensory ligaments, also known as zonules. The chamber between the posterior cornea and the front surface of the capsular bag is commonly referred to in the art as the anterior chamber, which contains a fluid known as the aqueous humor. A posterior chamber, filled with vitreous humor, is behind the anterior chamber, and includes the capsular bag and the physiological crystalline lens.

Light entering the eye through the cornea is converged by the crystalline lens towards the retina, and more particular to a central part of the retina known as the macula, arriving at a point focus known as the fovea. The cornea and tear film are responsible for the initial convergence of entering light. Subsequent to refraction by the cornea, the light passes through the physiological crystalline lens, where the light is refracted again. When focusing on an object, ideally the physiological crystalline lens refracts incoming light towards a point image on the fovea of the retina. The amount of bending to which the light is subjected is termed the refractive power. Generally, an RDC involves damage to the fovea, and can spread into the macula. In most patients, even in those with advanced macular degeneration, the macula is not completely damaged, but retains healthy or functional areas.

The person who suffers from a RDC is typically treated optically by using magnification or prism in lens form. At distance, a Galilean telescopic magnifying device may be placed in front of the eye or in the eye and customized to the user's needs. The magnification of the device enlarges the image viewed, expanding the image into more healthy areas of retina peripheral (eccentric) to the scotoma. At near, the person suffering from a RDC usually needs magnification in the form of magnifying plus powered lenses and/or prisms—the former (i.e., the plus lenses and magnifiers) to help enlarge the image outside of the scotoma as in the telescopic example and the latter (e.g., the prisms) to help shift the images to different, more functional areas of the retina.

The prismatic lens approach typically involves mounting a prism in an eyeglass frame. The prism is designed to redirect incoming or incident light rays, thereby angling the departing rays into healthy or functional portions of the retina. Angling the light rays in this manner shifts the scotoma out of the visual line of sight. It has been theorized to place a prism in an intraocular lens replacing the natural or physiological lens of the eye. Examples of theoretical, implantable prismatic lens devices are found in U.S. Pat. Nos. 5,728,156, 5,683,457, and 4,581,031, which disclose using prism wedges for shifting light away from the diseased center of the retina to a functional portion, and purportedly thereby restoring the central field vision to a patient.

The addition of a prism wedge to an intraocular lens would increase the overall thickness of the optic. The thickness of the prism wedges of such theoretical devices would need to be sufficient to permit redirection of the image a sufficient distance (or diopter) away from the damaged portion of the macular, to a healthy area of the retina. However, the relatively large thickness required of an intraocular prism to attain such an image shift would be problematic in several respects. Implantation of a thick prism carries certain surgical risk. During implantation of a thick prism-containing lens, the capsular bag intended to hold the lens would be susceptible to breakage and tearing, which would necessitate removal of the lens and vitrectomy and create risk of ultimately more macular damage. Further, the insertion incision for creating an opening to receive a thick prism-containing lens would be larger than required with a thinner prism-containing lens. Another drawback is a thick prism lens would preclude a second device from being implanted in the capsular bag to enhance magnification and/or allow for minification, such as in the case of creating a Galilean telescopic effect.

Another visual defect afflicting a large segment of the population is known generally as strabismus or binocular misalignment. A person's processing of viewed three-dimensional objects depends on proper alignment of the eyes. When both eyes are properly aligned and targeted on the same object, a single object is viewed. On the other hand, when one eye turns inward, outward, upward, or downward, two different pictures are sent to the brain, causing loss of depth perception and binocular vision.

Strabismus, more commonly referred to as cross-eye, generally is characterized by a misalignment of the eyes. Esotropia, the most common form of strabismus, involves deviations in which the eyes are misaligned inwards, and more specifically one eye deviates inward while the other fixates normally. With esotropia, visual axes are turned inward so that they cross when focused on distance objects. (The visual axis is described as the axis of the eye that extends directly outward from the macula through the visual axis of the cornea towards optical infinity.) Another form of strabismus known as exotropia involves a condition in which one eye deviates outward so that the eyes do not cross when focused on distant objects.

Binocular function is commonly restored in patients with strabismus using prismatic lenses designed to realign images toward the binocular retinal locus. For example, eso-deviations as corrected by placing eyeglasses with a "base-in" prism lens in front of the eye. Exo-deviations are corrected by placing eyeglass with a "base-out" prism lens in front of one or both of the eyes. Vertical deviations, where the plane(s) of one or both eyes are not aligned in the vertical direction, are corrected with "base-up" or "base-down" prism(s) in the eyeglasses. A drawback of these conventional solutions is that the user becomes dependent upon eyeglasses.

SUMMARY OF THE INVENTION

In accordance with the purposes of the invention as embodied and broadly described herein, an aspect of the invention provides an intraocular device comprising a prism having a first index of refraction ($n_1$), and a shift amplifier having a second index of refraction ($n_2$) differing from the first index of refraction ($n_1$). A first ratio (equal to the greater of the first index of refraction ($n_1$) and the second index of refraction ($n_2$) divided by the lesser of the first index of refraction ($n_1$) and the second index of refraction ($n_2$)) is greater than a second ratio (equal to the greater of the first index of refraction ($n_1$) and an index of refraction of water ($n_3$) divided by the lesser of the first index of refraction ($n_1$) and the index of refraction of water ($n_3$)).

According to another aspect of the invention, an intraocular device comprising a lens, a prism, and a shift amplifier is provided. The prism comprises an anterior face and a posterior face, and has a first index of refraction ($n_1$). Between the prism and lens is a chamber in which the shift amplifier is located. The shift amplifier has a second index of refraction ($n_2$) differing from the first index of refraction ($n_1$). Preferably, a first ratio (equal to the greater of the first index of refraction ($n_1$) and the second index of refraction ($n_2$) divided by the lesser of the first index of refraction ($n_1$) and the second index of refraction ($n_2$)) is greater than a second ratio (equal to the greater of the first index of refraction ($n_1$) and an index of refraction of water ($n_3$) divided by the lesser of the first index of refraction ($n_1$) and the index of refraction of water ($n_3$)).

According to another aspect of the invention, a method is provided for correcting vision in a patient with central field loss. The method comprises implanting the intraocular device of either of the above aspects into an eye of the patient with central field loss, the prism and shift amplifier of the intraocular lens cumulatively shifting a retinal image away from the fovea of the eye to a functional retinal portion of the eye of the patient.

According to still another aspect of the invention, a method is provided for restoring binocular function of a patient with a binocular misalignment, the method comprising implanting the intraocular device into an eye of a patient with binocular misalignment, the prism and shift amplifier of the intraocular lens cumulatively aligning an image towards the binocular retinal locus to restore binocular function.

In accordance with a further aspect of the invention, a system is provided for improving visual function in the eye of a patient with central field loss. The system comprises the intraocular device of the present invention used in combination with an adjunct lens, which may be a synthetic lens or the physiological crystalline lens.

BRIEF DESCRIPTION OF THE DRAWINGS

The accompanying drawings are incorporated in and constitute a part of the specification. The drawings, together with the general description given above and the detailed description of the preferred embodiments and methods given below, serve to explain the principles of the invention. In such drawings:

FIG. 1 is a schematic representation of an eye having a posterior chamber implanted with an intraocular device of an embodiment of the invention;

FIG. 2 is an enlarged schematic side sectional view of the intraocular device of FIG. 1;

FIG. 3 is a schematic bottom plan view of an anterior lens and associated chamber of the intraocular device of FIGS. 1 and 2;

FIG. 4 is an exploded, schematic side sectional view of the intraocular device of FIGS. 1 and 2;

FIGS. 5 through 12 are schematic side sectional views of intraocular devices according to additional embodiments of the invention;

Figure 13:
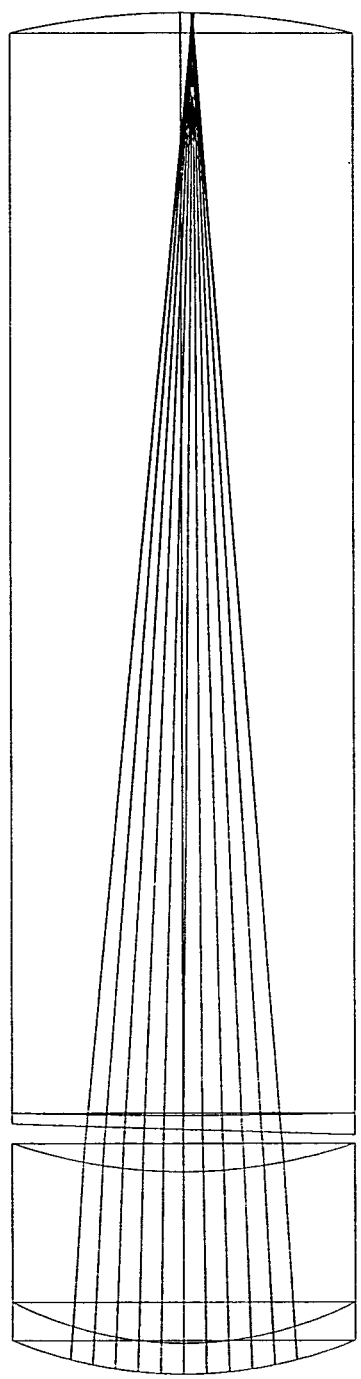
FIG. 13 is a ray trace for the embodiment of FIGS. 1-4, modified to produce a 1 diopter shift.

DETAILED DESCRIPTION OF THE PREFERRED EMBODIMENTS AND PREFERRED METHODS OF THE INVENTION

Reference will now be made in detail to the presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

It is to be noted that, as used in the specification and the appended claims, the singular forms "a," "an," and "the" include plural referents unless the context clearly dictates otherwise.

For the purposes of this disclosure, all refractive indexes are measured at 25° C. and 550 nm (visible light).

FIGS. 1 through 4 illustrate an intraocular device, generally designated in FIG. 2 by reference numeral 130, according to a first embodiment of the invention. Intraocular device 130 is sized and configured to be received in an eye, preferably a human eye 100. As embodied in FIG. 1, intraocular lens 130 is sized and configured to be received in capsular bag 102 in posterior chamber 112 of human eye 100. Although not shown, it is within the scope of the invention to place the intraocular device embodied herein in other regions of the eye. For example, the intraocular device embodied herein may be inserted into anterior chamber 110 of eye 100 in which the physiological lens has or has not been removed, the ciliary sulcus, iris fixated. Such positioning of the intraocular device might be desirable, for example, in the case of a person suffering from a retinal degenerative condition but having no cataract, in which case it is desirable to keep the physiological crystalline lens intact. Device 130 may be placed in one eye or both eyes of the patient.

In order to facilitate the description of the invention, additional elements of human eye 100 will now be described with reference to FIG. 1. Eye 100 includes optically transmissive cornea 104, behind which is iris 106. The pupil (unnumbered) is interior to the iris 106 and commonly appears as a black circular area concentrically inward of the iris 106 when viewed from directly in front of eye 100. Anterior chamber 110 is generally defined as the area between posterior cornea 104 and the front surface of capsular bag 102. Posterior chamber 112 is the area behind anterior chamber 110, and includes capsular bag 102 and a physiological crystalline lens, which is not shown but is replaced in FIG. 1 by intraocular device 130. Ciliary muscle 108 surrounds capsular bag 102, and zonules couple ciliary muscle 108 to the physiological crystalline lens. Posterior chamber 112 behind capsular bag 102 contains vitreous humor, which is interior to sclera 114. Coating sclera 114 is the conjunctiva (not shown). In a healthy eye, light enters cornea 104 and passes through the pupil before reaching the physiological crystalline lens, which converges light on retina 116 at the macula, and more particularly at fovea 118.

Intraocular device 130 comprises a prism 132 illustrated as a wedge-shaped object. Prism 132 of the first embodiment is illustrated as having a right-angle triangular cross-sectional profile, in which anterior face 134 is oblique to optical axis 122 and posterior face 136 of prism 132 is perpendicular to optical axis 122, which is generally coincident with the axis of device 130. It should be understood that various other prisms and prism shapes may be employed. For example, although not shown in the figures, the prism may be truncated or chamfered. Also, alternative prismatic devices, such as a fresnel prism, may be selected as the prism. Other profiles and shapes also are possible. Anterior and posterior faces 134 and 136 optionally possess unequal lengths without forming a right angle, and/or may be inverted from the position shown in FIGS. 1 through 4. Further, prism 132 may comprise a single, unitary piece or a plurality of pieces (FIG. 9). These are just some examples of variations and modifications possible to the prismatic element (e.g., prism 132) of the invention.

An anterior lens 140 and a posterior lens 142 are positioned at anterior face 134 and posterior face 136, respectively. Although lenses 140 and 142 are shown concentric with optical axis 122, it should be understood that either lens may be tilted relative to optical axis. For example, in FIG. 2 posterior lens 142 may be tilted so that its axis (defined between vertices) is coincident with the central axis of departing rays as shifted by prism 132. The relative positioning of lenses 142 and 142 may be determined based on usage and any aberrations to be accounted for.

Anterior lens 140 body, shown in isolated view in FIG. 3, has a posterior surface with a recessed chamber 146. As best shown in FIG. 3, recessed chamber 146 may be of a simple shape, such as a circle concentric with the periphery of anterior lens 140, although polygonal (e.g., square or rectangular), oval, and random shapes are possible for chamber 146. Surrounding and defining the periphery of recessed chamber 146 is lip 148, best shown in FIGS. 3 and 4. In FIG. 3 the anterior surface of lens 140 is illustrated as having a generally spherical shape. Posterior lens 142 has a matching shape. However, it is within the scope of this invention to provide anterior lens 140 and posterior lens 142 with different spherical radii or aspheric or other shapes, for example, to compensate for aberrations such as astigmatism.

In the embodiment illustrated in FIGS. 1 through 4, anterior lens 140 and posterior lens 142 are both convex. It is to be understood, as described and illustrated for example in additional embodiments below, either anterior lens 140 or posterior lens 142 (or both lenses 140 and 142) may be concave to give intraocular device 130 an overall convex-convex, convex-concave, concave-convex, or concave-concave appearance, depending upon the particular refractive needs of the individual and the intended use of device 130. Additionally, anterior lens 140 and/or posterior lens 142 may have a non-curved or flat surface with a radius of curvature equal to infinity, as shown in FIG. 11.

Prism 132, anterior lens 140, and posterior lens 142 may be made of the same or different materials from one another, although each preferably is optically transparent. It is within the scope of the invention for prism 132, anterior lens 140, and/or posterior lens 142 to possess a tint of any color that is not dense enough to significantly impede the transmission of light or the intended objects of this invention. Each of prism 132 and lenses 140 and 142 preferably comprises a material or materials biologically compatible with the human eye, and capable of injection molding, lathing, the like, or other processes used for manufacturing intraocular lenses, as known in the art. In particular, the materials are preferably non-toxic, non-hemolytic, and non-irritant. The material preferably undergoes little or no degradation in optical performance over its period of use. For example, the material may be rigid and/or biocompatible, such as, for example, polymethylmethacrylate (PMMA), or flexible and deformable, such as silicones, deformable acrylic polymeric materials, hydrogels and the like which enable intraocular device 130 to be rolled, deformed, or folded for insertion through a small incision into the eye during implantation. The above list is merely representative, not exhaustive, of the possible materials that may be used in this invention. For example, collagen or collagen-like materials, e.g., collagen polymerized with a monomer or monomers, may be used to form prism 132, anterior lens 140, and/or posterior lens 142. However, it is possible to make the lenses of a material or materials, e.g., elastic, adapted for folding or deformation to facilitate insertion of intraocular device 130 into eye 100.

Surfaces of anterior and posterior lenses 140 and 142 may be modified with heparin or other types of surface modification designed to increase biocompatibility and decrease possibility of capsular haze occurring. The lenses may also include a "ledge" for reducing formation of capsular haze.

Situated in recessed chamber 146 of anterior lens 140 is a shift amplifier 150 interposed between anterior lens 140 and prism 132. Shift amplifier 150 is depicted in FIGS. 1, 2, and 4 as having a wedge-shaped profile substantially identical to, yet inverted with respect to prism 132. The front face of shift amplifier 150 is in contact with the recess-defining surface of anterior lens 140, and the rear face of shift amplifier 150 is in contact with prism 132 to establish a shift amplifier/prism interface. As shown in FIG. 4, shift amplifier 150 appears as a solid.

Generally, suitable shift amplifiers are those materials that, when placed next to an oblique face of a prism, provide a change or "shift" in angle between light rays incident on a prism and light rays departing the prism that is greater than the shift that would have been obtained for water placed next to the oblique face of the prism. Stated differently, a first ratio (equal to a quotient of the greater of the first index of refraction ($n_1$) and the second index of refraction ($n_2$) divided by the lesser of the first index of refraction ($n_1$) and the second index of refraction ($n_2$)) is greater than a second ratio (equal to a quotient of the greater of the first index of refraction ($n_1$) and an index of refraction of water ($n_3$) divided by the lesser of the first index of refraction ($n_1$) and the index of refraction of water ($n_3$)).

Shift amplifier 150 may comprise, and optionally consists essentially of or consists of, a gas, a liquid, or a combination of gas and liquid, in which case the shift amplifier fluid preferably fills recessed chamber 146 defined between prism 132 and lens 140. Shift amplifier 150 alternatively may comprise a solid, alone or together with a gas and/or liquid. Shift amplifier 150 optionally may comprise a vacuum. Air is preferred. Other gases that may be selected as shift amplifier 150 include nitrogen, argon, and neon. Representative liquids that may be selected as shift amplifier 150 in chamber 146 include perfluorocarbons. Representative solids include coatings such as metal oxides (e.g., titanium oxide, zirconium oxide) and metal nitrides (e.g., titanium nitride, boron nitride). Another example of a solid potentially of use is zinc sulfide. Solid coatings may be applied using vapor deposition, vacuum coating, or other suitable techniques, and may form a single or multiple-layered structure.

As embodied in FIGS. 1-4, the posterior face of shift amplifier 150 abuts against and interfaces anterior face 134 of prism 132, so that shift amplifier 150 posterior face is set at the same oblique angle to visual axis 122 as anterior face 134. The front face of shift amplifier 150 is shown in the illustrated embodiment as perpendicular to visual axis 122 for the purpose of simplifying design. It should be understood that other configurations are possible. For example, shift amplifier 150 front face may be arranged differently, i.e., non-perpendicular to optical axis 122. As further examples of possible alterations and modifications, shift amplifier 150 may be truncated, chamfered, or possess a shape other than that of a wedge. However, the front face of shift amplifier 150 preferably is non-parallel to shift amplifier 150 posterior face and anterior face 134.

Returning to FIGS. 1 through 4, light entering intraocular device 130 along optical axis 122 travels through cornea 104 and through the pupil. In a healthy eye containing a physiological crystalline lens, cornea 104 and the lens focus the incoming light onto the macula at a point called fovea 118 for processing. However, in a person suffering from central field vision loss, such as encountered with degenerative retinal conditions, the macula is damaged and not capable of properly processing the incoming light rays into a viewable image. A prismatic lens, such as prism 132 replacing the physiological lens, redirects the incoming light rays away from the damaged area of the macula. However, prism wedges of conventional devices possess relatively large thicknesses in order to redirect light a sufficient number of diopters away from fovea 118 into a healthy area of retina 116. As discussed above, the relatively large thickness of a conventional prism can lead to a multitude of problems.

In accordance with the embodiment illustrated in FIGS. 1 through 4 and other embodiments of the invention, the shift amplifier, such as shift amplifier 150, circumvents the need for a thick prism and thereby overcomes problems of conventional prism lenses. More specifically, light passing through intraocular device 130 implanted in eye 100 intersects shift amplifier 150 before passing through prism 132. Juxtaposition of shift amplifier 150 adjacent prism 132 enhances the prismatic effect of device 130.

Generally, prismatic effect may be calculated as follows. Assume a prism with an anterior surface that is normal to the incident light. The posterior side is angled with respect to the incident light. The equation that gives the angular deviation of the light (with respect to the original incident beam) from this prism is given by:

$$\alpha = \sin^{-1}(n_b \sin \phi / n_a) - \phi \quad (1)$$

In this equation, $\alpha$ is the angular deviation of the beam exiting the prism with respect to the beam incident to the anterior face of the prism. For the purpose of equations (1) through (4), the index of refraction of the prism is given by $n_b$, and the index of refraction of the surrounding medium (e.g., vitreous fluid of the eye) is given by $n_a$. The wedge angle of the prism is given by $\phi$.

To determine the diopter value, d, obtained for a given wedge angle, and vice versa to determine the necessary wedge angle for producing a desired diopter value d, the following equation is used:

$$d = 100 \tan(\alpha) \quad (2)$$

or $$d = 100 \tan(\sin^{-1}(n_b \sin \phi / n_a) - \phi) \quad (3)$$

The thickness of the prism to achieve this diopter value is dependent on the beam diameter (or pupil diameter). The thick side of the prism is at least the following value:

$$t = b \tan(\phi) \quad (4)$$

wherein b is the beam (or pupil) diameter. In practice, t is slightly thicker than this value so that it is easier to fabricate and will be less sensitive to position errors when placed in the eye (to assure the entire beam goes through the prism).

So, for a given diopter value desired of a prism, the thickness is calculated by determining $\phi$ based on known index of refraction of vitreous fluid $n_a$ and known index of refraction of prism $n_b$. In the event that $\phi$ and either of $n_a$ or $n_b$ are unknown, equation (1) may be solved iteratively. An iterative approach might involve, for example, estimating angle $\phi$ and either of the refractive indices to solve for diopter, then adjusting one or both of the estimations based on variation between the calculated diopter and the desired diopter.

For the inventive device, the material (and corresponding refractive index) of shift amplifier 150 is substituted for that of the vitreous fluid. As evident from the above equations, increasing the ratio between refractive indices of the prism 132 and shift amplifier 150 increases the angular deviation $\alpha$ of the beam departing prism posterior surface 136 with respect to the beam incident on prism anterior surface 134. Thus, for a given angular deviation $\alpha$, increasing the ratio between $n_a$ and $n_b$ permits a smaller the prism angle $\phi$ (and hence a smaller prism thickness) for obtaining a given diopter value d.

With the above principals in mind, the refractive index $n_2$ of shift amplifier 150 is selected to provide a first ratio (defined as a quotient of the greater of the refractive index of shift amplifier 150 and the refractive index of prism 132 divided by the lesser of the refractive indices of shift amplifier 150 and prism 132) that is greater than a second ratio (defined as a quotient of the greater of the refractive indices of prism 132 and the surrounding fluid (vitreous humor) divided by the lesser of the refractive indices of prism 132 and the vitreous humor).

Typically, prism 132 is made of a material having a refractive index $n_1$ greater than the refractive index $n_3$ of water (1.334). For such typical cases, if a low refractive index material (e.g., as gas) is selected (i.e., if shift amplifier 150 has a second index of refraction ($n_2$) that is less than the first index of refraction ($n_1$) of prism 132), then the second index of refraction of this embodiment is selected to be lower than that of water, so that the first ratio ($n_1/n_2$) of the first index of refraction ($n_1$) to the second index of refraction ($n_2$) is greater than the second ratio ($n_1/n_3$) of the first index of refraction ($n_1$) to an index of refractive of water ($n_3$), that is if $n_2<n_1$, then $n_2$ is selected to satisfy $n_1/n_2 > n_1/n_3$.

More preferably, the index of refraction of shift amplifier 150 of the embodiment of the preceding paragraph is less than 1.25, optionally less than 1.15, and optionally less than 1.10. An exemplary gas is air, which has an index of refraction of 1. For example, the ratio of the refractive index of a polymethylmethacrylate (PMMA) prism (1.492) to air (1.0) is 1.492, which is greater than the refractive index of a PMMA prism to water, i.e., 1.492/1.334, which is 1.118. Shift amplifier 150 produces a greater refractive index ratio, which in turn generates a greater diopter value d than achieved by a conventional prism device of identical thickness adjacent to water. Thus, shift amplifier 150 permits device 130 to generate a given diopter value d using a much thinner prism 132 than required by a conventional prism device to achieve the same diopter value d.

Figure 14:
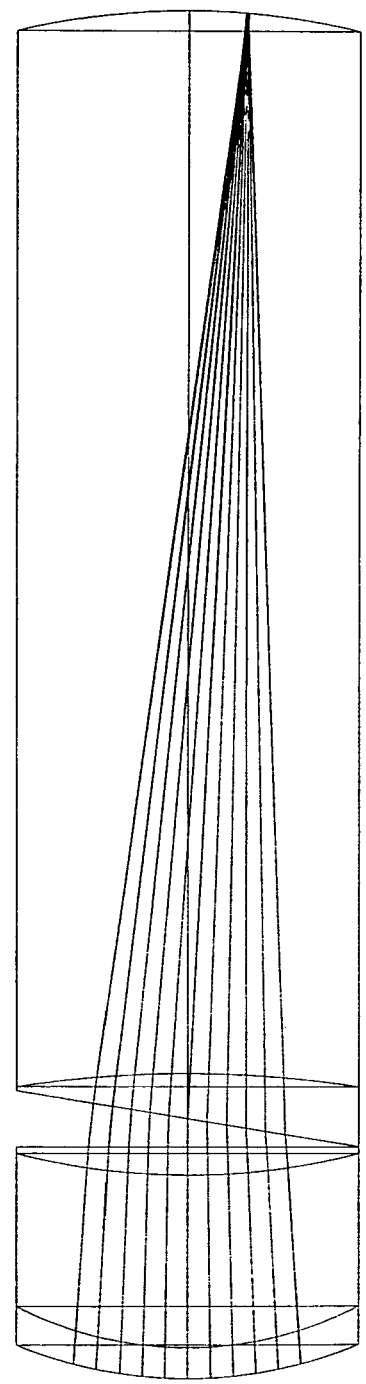
FIG. 14 is a ray trace for the embodiment of FIGS. 1-4, modified to produce a 5 diopter shift.

For typical prism materials having a refractive index $n_1$ greater than the refractive index $n_3$ of water, if a higher refractive index material (e.g., a solid) is selected (i.e., if shift amplifier 150 has a second index of refraction ($n_2$) that is greater than the first index of refraction ($n_1$) of prism 132), then the second index of refraction should be sufficiently high to provide a first ratio ($n_2/n_1$) of the second index of refraction ($n_2$) to the first index of refraction ($n_1$) that is greater than the second ratio ($n_1/n_3$) of the first index of refraction ($n_1$) to the index of refraction of water ($n_3$), that is if $n_2>n_1$, then $n_2$ is selected to satisfy $n_2/n_1 > n_1/n_3$ Visualization of this principal in the context of an embodied method of the invention is furthered with reference to FIGS. 1, 13, and 14. In FIG. 1, light rays departing from intraocular device 130 are shifted away from fovea 118 to healthy area 128 of retina 116. FIGS. 13 and 14 represent calculated ray traces for optical systems comprising intraocular device 130 with a prism and shift amplifier designed for a 1 diopter shift and a 5 diopter shift, respectively. A comparison of these calculated ray traces demonstrates how prism thickness and the use of a shift amplifier effect diopter value d away from the optical axis.

The width, height, and depth of intraocular device 130 will depend upon several factors, including the sizes of the patient's physiological lens, anterior chamber, and posterior chamber. Generally, the width and height of the lens body may be, for example, in a range of 2.5 mm to 10 mm, more commonly 4.0 mm to 7.5 mm. The width (w) and height (h) are preferably, but not necessarily, the same in dimension. The depth (d) or thickness of the lens body should not be so great as to inhibit implantation into the eye. The depth (d) may be, for example, at least 0.9 mm. The above dimensions are provided by way of example, and are not exhaustive or exclusive.

According to calculations, an intraocular device having the configuration shown in FIG. 2, and having air as the shift amplifier with a 4 mm pupil diameter, would require a thickness of only 1.0 mm to generate a one (1) diopter (0.2 mm) prismatic shift away from the fovea. The same intraocular device would require thicknesses of only 1.2 mm and 1.5 mm to attain prismatic shifts of three (3) diopters (0.6 mm) and five (5) diopters (1.0 mm), respectively. For the same intraocular device comprising a shift amplifier of liquid with refractive index (n) of 1.22, prismatic shifts of 1, 3, and 5 diopters can be accomplished with prism thicknesses of 1.2 mm, 1.5 mm, and 1.7 mm, respectively. For comparative purposes, the same intraocular device without a shift amplifier (i.e., surrounding water) would require thicknesses of 1.2 mm, 1.7 mm, and 2.4 mm to obtain prismatic shifts of 1, 3, and 5 diopters, respectively.

Additional embodiments of the invention will now be described with reference to FIGS. 5 through 12. In the interest of brevity, the below discussion will be limited mostly to differences between these additional embodiments and the embodiment of FIGS. 1-4. The description of the various materials, principals, elements, etc. provided above with regard to the first embodiment is incorporated into the description of each of the below additional embodiments. It should be understood that each embodiment is implantable into an eye, such as a human eye, as depicted in FIG. 1 or otherwise as discussed herein.

FIG. 5 depicts an intraocular device 530 comprising an anterior lens 540, a prism 532, and a shift amplifier 550 interfacing prism 532. Unlike the embodiment of FIGS. 1-4, device 530 is free of a posterior lens. Although not shown, the device may be embodied to comprise a posterior lens but no anterior lens, with prism 532 and shift amplifier 550 exchanging positions.

FIG. 6 embodies an intraocular device 630 comprising an anterior lens 640 and a posterior lens 642. Unlike the embodiment of FIGS. 1-4, prism 632 and shift amplifier 650 are housed in a recessed chamber of posterior lens 642. Also, prism 632 is positioned in front of shift amplifier 650.

Figure 15:
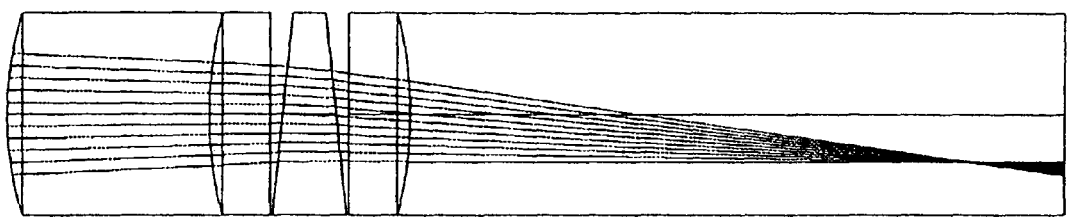
FIG. 15 is a ray trace for the embodiment of FIG. 7.

FIG. 7 depicts an embodiment of an intraocular device 730 comprising an anterior lens 740 and a posterior lens 742 defining respective recesses that cooperate with one another to form a recessed chamber (unnumbered). A prism 732 is received in the recessed chamber. Prism 732 possesses an isosceles triangular profile, such that neither the anterior face nor the posterior face of prism 732 is orthogonal to a central axis of device 730. Adjacent and interfacing the anterior face of prism 732 is an anterior shift amplifier 750. A posterior shift amplifier 752 is positioned adjacent and interfaces the posterior face of prism 732. Anterior shift amplifier 750 and posterior shift amplifier 752 each have a respective refractive index, which may be the same as or different than one another. The refractive index or indices of amplifiers 750 and 752 are preferably less than the refractive index of prism 732. A ray trace of device 730 is shown in FIG. 15. A greater calculated diopter value was obtained by placing shift amplifiers 750 and 752 in front of and behind prism 732.

FIGS. 8 and 9 illustrate intraocular devices having a concave-concave configuration. In FIG. 8, intraocular device 830 comprises a concave anterior lens 840 and a concave posterior lens 842. Prism 832 and shift amplifier 850 are each housed in a chamber of anterior lens 840. Intraocular lens 930 of FIG. 9 is similar to that of FIG. 7, except that anterior and posterior lenses 940 and 942 are each concave, and side-by-side dual prisms 932 and 933 are provided in place of a unitary prism. Shift amplifiers 950 and 952 are located on opposite sides of prisms 932 and 933. FIG. 10 illustrates a convex-concave intraocular device 1030. In FIG. 11, intraocular device 1130 comprises a posterior capsule (or lens) 1142 lacking curvature.

FIG. 12 illustrates an intraocular device 1230 comprising a prism 1232 and a shift amplifier 1250. In the embodiment of FIG. 12, shift amplifier 1250 comprises a solid or other material not requiring a surrounding chamber, such as a coating applied to posterior surface of prism 1232. The illustrated embodiment of FIG. 12 is free of an anterior or posterior lens, although this embodiment may be modified to include an anterior lens and/or posterior lens.

Various combinations and modifications of the above-described embodiments are contemplated and would be understood to those skilled in the art having reference to this disclosure.

Several of the above-described embodiments include curved lenses anterior and/or posterior to the prism and shift amplifier for providing the intraocular device with a desired power. For example, in the event the intraocular device is placed in the capsular bag, it is possible to add positive (converging) power to the eye by use of a convex shell (lenses) surrounding the prism and shift amplifier.

According to another aspect of the invention, the inventive intraocular device is used in combination with at least one adjunct lens providing the desired power and optionally magnification. The intraocular device and the adjunct lens together form a visual correction system, in which the intraocular device is either with or without power (curvature).

According to one embodiment of the visual correction system, the adjunct lens comprises the physiological lens, in which case the inventive intraocular device is positionable, for example, in the anterior chamber, the ciliary sulcus, or the iris fixated. This embodiment is particularly preferred where the physiological crystalline lens is not damaged.

Figure 16:
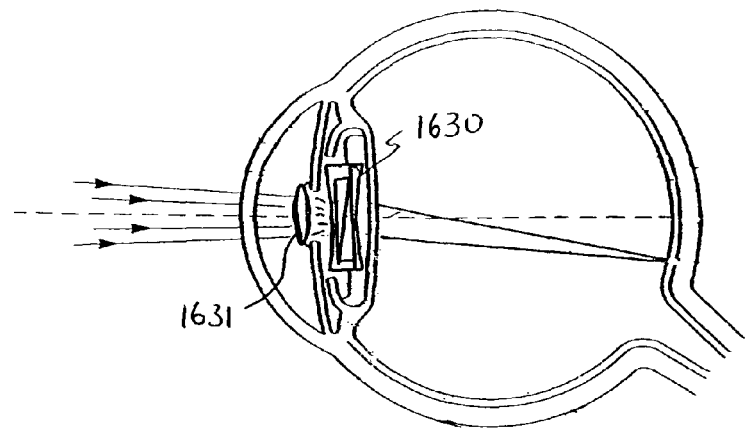
FIG. 16 is a schematic representation of an eye having a vision correction system according to an embodiment of the invention.

According to another embodiment of the visual correction system, a synthetic adjunct lens is placed in front of or behind the inventive intraocular lens. According to an example of this embodiment, the inventive intraocular device is placed in the posterior chamber, more preferably the capsular bag, and the adjunct lens is placed for example in the anterior chamber of the eye, as shown in FIG. 16, or vice versa. Optionally, the adjunct lens may comprise a lens exterior to the eye, such as a contact lens or eyeglasses.

According to an embodied method of the invention, the visual correction system is implanted into the eye of a person with central vision loss for facilitating treatment of RDC. The patient is preferably first examined to determine the central vision loss, including any geographic atrophy extending beyond the fovea. Such examinations are well within the purview of a person skilled in the art, and may be performed, for example, using conventional prism lenses. The necessary or desired dimensions of the prism of the intraocular lens may then be determined by calibrating the vertex distance for the implanted device and using the above equations.

As an example, a RDC is treatable by providing the intraocular device of the present invention as the ocular lens of a Galilean-type device, and further providing an adjunct objective lens in front of the ocular lens for establishing a telescopic benefit and a near-magnifying benefit. The Galilean positive objective lens 1631 comprises, for example, an eyeglass lens, contact lens, and/or an implant in front of the ocular lens 1630, as shown in FIG. 16. The telescopic benefit is derived from the effective power of the ocular lens in straight-ahead gaze being calculated to be negative in power, and the objective lens in front of the ocular lens being calculated to be positive in power. The negative power of the ocular lens is controlled through selection of the lens curvatures of the ocular lens. As referred to herein and generally understood in the art, a "negative power" lens is a "diverging lens", i.e., a lens having a cumulative effect of diverging light passing through the lens. On the other hand, a "positive power" lens is a "converging lens", i.e., a lens having a cumulative effect of converging light rays passing through the lens.

By controlling the spacing and focal lengths of the ocular lens and the objective lens, magnification can be obtained, if desired. Preferably, the focal points and/or focal planes of the objective and ocular lenses are coincident with one another, as is the case in a Galilean telescope. The combination of the negative ocular (intraocular) lens and the positive objective lens (together with the power provided by cornea) creates a telescopic power of a Galilean type, provided the focal planes of ocular and objective are sufficiently coincident. Alternatively, the inventive device and adjunct lens serve as the objective and ocular lenses of the Galilean system, respectively.

In preferred embodiments of the invention, the iris of the natural eye in essence functions as the "housing" of the ocular of the telescope, thereby removing the need for combining the intraocular lens with an artificial housing, such as those used in conventional implanted telescopic devices. Advantageously, omission of an artificial ocular housing can improve the field of vision of a person afflicted with a RDC. For example, the artificial housing of a telescope typically is sized and positioned away from the iris in such a manner as to limit the field of vision, providing a field of vision lesser than that obtainable by the naked eye. Further, the artificial housing of a telescope is not able to account for subtle variations in pupil size due to pupil dilation (e.g., for far vision) and pupil restriction (e.g., for near vision). In embodiments of the present invention in which the iris functions as the telescopic housing of the ocular, the user's field of view is not unduly restricted.

According to still another embodiment of the invention, the left and right eyes of the patient have different visual correction systems. For example, it is possible to use ocular devices providing different levels of magnification between eyes. Optionally, the adjunct lens may comprise the intraocular lens disclosed in U.S. Pat. No. 6,855,164 and U.S. patent application Ser. No. 11/007,345, the complete disclosures of which are incorporated herein by reference.

Another embodiment of the invention comprises a method of treating binocular misalignment with the inventive intraocular device described herein. In this method, it is preferred to use the intraocular device as the adjunct lens in combination with the physiological crystalline lens, with the adjunct lens placed in the anterior chamber of the eye. Alternatively, the inventive intraocular lens may replace the physiological crystalline lens, although removal of the physiological crystalline lens usually is not desirable unless the lens is somehow damaged, which is not usually the case for patients afflicted with strabismus. The appropriate wedge angle of the prism may be determined by measuring the degree of eye turn/deviation, as generally known in the art using, for example, prismatic lenses, and applying the equations above.

The intraocular devices of the present invention may be formed using conventional molding (e.g., injection or compression) processes and/or lathing techniques. Coupling of the lenses to one another and/or to the prism(s) also may comprise conventional techniques, such as laser welding or other means. Alternatively, the lenses may be injection molded or otherwise formed as a unitary piece. Introduction of a fluid into a recessed chamber of the lens(es) may be performed prior or subsequent to insertion of the prism into the recessed chamber, and prior or subsequent to attachment of the lenses to one another, if applicable. For example, in the embodiment of FIGS. 1-4 prism 132 may be inserted into recessed chamber 146 of anterior lens 140 to leave a space for introduction of shift amplifier 150. An entry port and optionally an exhaust port may be provided in anterior lens 140 for permitting introduction of a fluid (gas or liquid) through the entry port and venting of air through the exhaust port. After shift amplifier 150 is introduced into the chamber, the entry and exhaust ports are closed to enclose the chamber.

As described in connection with the embodiments above, the intraocular device can be inserted into the posterior chamber of the human eye, preferably into the capsular bag posterior to the iris to replace the physiological (natural) lens in the capsular bag positioned using known equipment and techniques. Posterior implantation is preferred in surgical procedures requiring removal of the physiological lens. By way of example, intra-capsular cataract extraction and IOL implantation utilizing clear corneal incision (CCI), phacoemulsification or similar technique may be used to insert the intraocular device after the physiological crystalline lens has been removed from the capsular bag. The incision into the eye may be made by diamond blade, a metal blade, a light source, such as a laser, or other suitable instrument. The incision may be made at any appropriate position, including along the cornea or sclera. It is possible to make the incision "on axis", as may be desired in the case of astigmatism. Benefits of making the incision under the upper lid include reduction in the amount of stitching, cosmetic appeal, and reduced recovery time for wound healing. The intraocular device is preferably rolled or folded prior to insertion into the eye, and may be inserted through a small incision, such as on the order of about 3 mm. It is to be understood that as referred to in the context of this invention, the term "capsular bag" includes a capsular bag having its front surface open, torn, partially removed, or completely removed due to surgical procedure, e.g., for removing the physiological lens, or other reasons. For example, in FIG. 1 the capsular bag has an elastic posterior capsule, and an anterior capsular remnant or rim defining an opening through which the physiological lens was removed.

Alternatively, the intraocular device may be inserted in the anterior chamber between the cornea and the iris. In an anterior chamber implant, the intraocular device is generally situated forward of, or mounted to, the iris.

In order to secure the intraocular device in place, the intraocular device also may comprise haptics, which is generally shown in FIG. 1 by reference numeral 120. Haptics 120 generally serve to anchor an optical body in place in the eye. Haptics are usually attached directly to a lens body. Various types of haptics are well known in the art, and their incorporation into this invention would be within the purview of an ordinary artisan having reference to this disclosure. Generally, the typical haptic is a flexible strand of nonbiodegradable material fixed to the lens body. By way of example, suitable haptics for this invention may be made of one or more materials known in the art, including polypropylene, poly(methyl methacrylate), and any biocompatible plastic or material in use now or in the future that are used to hold the lens in place. The haptics used with the invention may possess any shape or construction adapted or adaptable for use with this invention for securing the lens body in place in the eye. In the posterior chamber, the haptics secure the optical lens within the capsular bag, whereas in the anterior chamber haptics may extend into the area defined between the anterior iris and posterior cornea. It is also within the scope of this invention to use an "iris claw", which hooks onto the fibers of the iris, especially for anterior chamber intraocular lenses.

The foregoing detailed description of the preferred embodiments of the invention has been provided for the purposes of illustration and description, and is not intended to be exhaustive or to limit the invention to the precise embodiments disclosed. The embodiments were chosen and described in order to best explain the principles of the invention and its practical application, thereby enabling others skilled in the art to understand the invention for various embodiments and with various modifications as are suited to the particular use contemplated. It is intended that the scope of the invention cover various modifications and equivalents included within the spirit and scope of the appended claims.

What is claimed is:

1. An intraocular device, comprising:
a lens body sized to be received in the human eye, the lens body comprising an anterior lens having an optical axis, a posterior lens, and a chamber between the anterior lens and the posterior lens;
a prism situated in the chamber between the anterior and posterior lenses, the prism comprising a prism anterior face and a prism posterior face, at least one of the prism anterior face and the prism posterior face being oriented at an oblique angle relative to the optical axis for shifting incident light received from the anterior lens by an angular deviation with respect to the incident light so that light departing the posterior lens is converged to a focal point not coincident with the optical axis of the anterior lens, the prism having a first index of refraction ($n_1$); and
a shift amplifier having a second index of refraction ($n_2$) differing from the first index of refraction ($n_1$), the shift amplifier being situated in the chamber and adjacent to the prism,
wherein a first ratio of the greater of the first index of refraction ($n_1$) and the second index of refraction ($n_2$) divided by the lesser of the first index of refraction ($n_1$) and the second index of refraction ($n_2$), is greater than a second ratio of the greater of the first index of refraction ($n_1$) and an index of refraction of water ($n_3$) divided by the lesser of the first index of refraction ($n_1$) and the index of refraction of water ($n_3$).

2. The intraocular device of claim 1, wherein the second index of refraction $n_2$ is less than 1.334.

3. The intraocular device of claim 1, wherein the shift amplifier comprises a solid coating.

4. The intraocular device of claim 1, wherein the shift amplifier comprises a liquid.

5. The intraocular device of claim 1, wherein the shift amplifier comprises a gas.

6. The intraocular device of claim 5 wherein the gas is air.

7. The intraocular device of claim 1 wherein the shift amplifier abuts the anterior face of the prism.

8. The intraocular device of claim 1 wherein the shift amplifier abuts the posterior face of the prism.

9. The intraocular device of claim 1 wherein: the shift amplifier comprises a first shift amplifier abutting the anterior face of the prism; and the intraocular device further comprises a second shift amplifier abutting the posterior face of the prism.

10. The intraocular device of claim 1 wherein the second index of refraction is less than 1.10.

11. The intraocular device of claim 1, wherein the prism is shaped as a wedge.

12. The intraocular device of claim 11, wherein the anterior face is oblique to the optical axis and the posterior face is perpendicular to the optical axis.

13. The intraocular device of claim 11, wherein the posterior face is oblique to the optical axis and the anterior face is perpendicular to the optical axis.

14. The intraocular device of claim 1, wherein the anterior and posterior lenses are concentric with one another.

15. The intraocular device of claim 1, wherein the posterior lens has a posterior optical axis which is coincident with a central axis of the light departing the prism.

16. A method for correcting vision in a patient with central field loss, the method comprising:
implanting an intraocular device comprising a lens body sized to be received in the human eye, the lens body comprising an anterior lens having an optical axis, a posterior lens, and a chamber between the anterior lens and the posterior lens; a prism situated in the chamber between the anterior and posterior lenses, the prism comprising a prism anterior face and a prism posterior face, at least one of the prism anterior face and the prism posterior face being oriented at an oblique angle relative to the optical axis for shifting incident light received from the anterior lens by an angular deviation with respect to the incident light so that light departing the posterior lens is converged to a focal point not coincident with the optical axis of the anterior lens, the prism having a first index of refraction ($n_1$); and a shift amplifier having second index of refraction ($n_2$) differing from the first index of refraction ($n_1$), the shift amplifier being situated in the chamber and adjacent to the prism, wherein a first ratio of the greater of the first index of refraction ($n_1$) and the second index of refraction ($n_2$) divided by the lesser of the first index of refraction ($n_1$) and the second index of refraction ($n_2$), is greater than a second ratio of the greater of the first index of refraction ($n_1$) and an index of refraction of water ($n_3$) divided by the lesser of the first index of refraction ($n_1$) and the index of refraction of water ($n_3$), into an eye of a patient with central field loss, the prism and shift amplifier of the intraocular lens cumulatively shifting a retinal image away from the fovea of the eye to a functional retinal portion of the eye of the patient.

17. A method for restoring binocular function of a patient with a binocular misalignment, the method comprising:

implanting an intraocular device comprising a lens body sized to be received in the human eye, the lens body comprising an anterior lens having an optical axis, a posterior lens, and a chamber between the anterior lens and the posterior lens; a prism situated in the chamber between the anterior and posterior lenses, the prism comprising a prism anterior face and a prism posterior face, at least one of the prism anterior face and the prism posterior face being oriented at an oblique angle relative to the optical axis for shifting incident light received from the anterior lens by an angular deviation with respect to the incident light so that light departing the posterior lens is converged to a focal point not coincident with the optical axis of the anterior lens, the prism having a first index of refraction ($n_1$); and a shift amplifier having a second index of refraction ($n_2$) differing from the first index of refraction ($n_1$), the shift amplifier being situated in the chamber and adjacent to the prism, wherein a first ratio of the greater of the first index of refraction ($n_1$) and the second index of refraction ($n_2$) divided by the lesser of the first index of refraction ($n_1$) and the second index of refraction ($n_2$), is greater than a second ratio of the greater of the first index of refraction ($n_1$) and an index of refraction of water ($n_3$) divided by the lesser of the first index of refraction ($n_1$) and the index of refraction of water ($n_3$), into an eye of a patient with binocular misalignment, the prism and shift amplifier of the intraocular lens cumulatively aligning an image towards a binocular retinal locus of the patient to restore binocular function.

* * * * *